United States Patent
Hashmi et al.

(10) Patent No.: US 9,926,246 B2
(45) Date of Patent: Mar. 27, 2018

(54) INTEGRATED PROCESS FOR SIMULTANEOUS PRODUCTION OF OXO-ALCOHOLS AND PLASTICIZERS

(71) Applicant: SAUDI BASIC INDUSTRIES CORPORATION, Riyadh (SA)

(72) Inventors: Syed Azhar Hashmi, Riyadh (SA); Flaiyh Al-Anazi, Riyadh (SA); Abdullah Al-Nafissa, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/888,040

(22) PCT Filed: May 2, 2014

(86) PCT No.: PCT/IB2014/061163
§ 371 (c)(1),
(2) Date: Oct. 29, 2015

(87) PCT Pub. No.: WO2014/178031
PCT Pub. Date: Nov. 6, 2014

(65) Prior Publication Data
US 2016/0075621 A1    Mar. 17, 2016

Related U.S. Application Data (60) Provisional application No. 61/819,133, filed on May 3, 2013.

(51) Int. Cl.
| | | |
|---|---|---|
| C07C 67/08 | (2006.01) | |
| C07C 29/141 | (2006.01) | |
| B01J 23/72 | (2006.01) | |
| B01J 25/02 | (2006.01) | |
| B01J 31/20 | (2006.01) | |
| C07C 29/151 | (2006.01) | |
| C07C 45/50 | (2006.01) | |
| C07C 45/74 | (2006.01) | |
| B01J 19/00 | (2006.01) | |
| C07C 45/72 | (2006.01) | |

(52) U.S. Cl.
CPC ............ *C07C 29/141* (2013.01); *B01J 19/00* (2013.01); *B01J 23/72* (2013.01); *B01J 25/02* (2013.01); *B01J 31/20* (2013.01); *C07C 29/1516* (2013.01); *C07C 45/50* (2013.01); *C07C 45/72* (2013.01); *C07C 45/74* (2013.01); *C07C 67/08* (2013.01); *Y02P 20/125* (2015.11); *Y02P 20/127* (2015.11)

(58) Field of Classification Search
CPC ..... C07C 29/1516; C07C 45/50; C07C 45/74; C07C 67/08; C07C 31/12; C07C 31/125; C07C 47/02; C07C 47/21; C07C 69/80; C07C 29/141; C07C 45/72; B01J 19/00; B01J 23/72; B01J 25/02; B01J 31/20; Y02P 20/125; Y02P 20/127; H04W 8/18; H04W 8/183; H04W 8/20
See application file for complete search history.

(56) References Cited

U.S. PATENT DOCUMENTS

| | | | | |
|---|---|---|---|---|
| 3,077,500 | A | * | 2/1963 | Heinz ...................... B01J 31/08 521/32 |
| 3,487,112 | A | | 12/1969 | Paulik et al. |
| 3,527,809 | A | * | 9/1970 | Smith ..................... C07C 45/49 502/162 |
| 3,763,247 | A | | 10/1973 | Lemke et al. |
| 4,190,731 | A | | 2/1980 | Nehring et al. |
| 4,284,793 | A | * | 8/1981 | Sagara ..................... C07C 67/60 560/78 |
| 4,851,592 | A | * | 7/1989 | Morris ................... C07C 29/141 568/461 |
| 5,004,845 | A | | 4/1991 | Bradley et al. |
| 5,877,358 | A | | 3/1999 | Garton et al. |
| 6,455,743 | B1 | | 9/2002 | Ueda et al. |
| 7,232,934 | B2 | | 7/2007 | Saleh et al. |
| 7,582,802 | B2 | | 9/2009 | Caers et al. |
| 7,649,112 | B2 | | 1/2010 | Stevenson et al. |
| 2011/0312864 | A1 | | 12/2011 | Godwin et al. |
| 2012/0016159 | A1 | | 1/2012 | Liang et al. |

FOREIGN PATENT DOCUMENTS

| | | | |
|---|---|---|---|
| EP | 0052999 | * | 6/1982 |
| EP | 2390242 | * | 11/2011 |
| EP | 2390242 A2 | | 11/2011 |
| JP | 2012046429 A | | 3/2012 |
| WO | 9812162 A1 | | 3/1998 |
| WO | 2012008717 A2 | | 1/2012 |

OTHER PUBLICATIONS

Sharma et al. (The multi-step reactions for the synthesis of C8 aldehydes and alcohol from propene in a single pot using an eco-friendly multi-functional catalyst system: Kinetic performance for parametric optimization, Journal of Molecular Catalysis A: Chemical, 304, 33-39, published 2009).*
INEOS Polyolefins "Lavera," Ineos Ofefins & Polymers Europe (2007); 1 Page.
International Search Report for International Application No. PCT/IB2014/061163; International dated: May 2, 2014; dated: Jul. 25, 2014; 5 pages.
Machine Translation of JP2012046429; Filing Date Mar. 8, 2012; 62 Pages.
Written Opinion of the International Searching Authority for International Application No. PCT/IB2014/061163; International Filing Date: May 2, 2014; dated: Jul. 25, 2014; 6 Pages.

* cited by examiner

*Primary Examiner* — Yevegeny Valenrod
*Assistant Examiner* — Blaine G Doletski
(74) *Attorney, Agent, or Firm* — Cantor Colburn LLP (57) ABSTRACT

Disclosed herein are methods and systems for the simultaneous production of oxo-alcohols comprising n-butanol, isobutanol, and 2-ethylhexanol. Also disclosed are methods and systems for simultaneous production of plasticizers using the disclosed oxo-alcohols.

10 Claims, 3 Drawing Sheets

INTEGRATED PROCESS FOR SIMULTANEOUS PRODUCTION OF OXO-ALCOHOLS AND PLASTICIZERS

CROSS REFERENCE TO RELATED APPLICATIONS

This application is a 371 of International Application No. PCT/IB2014/061163, filed May 2, 2014, which claims priority to U.S. Patent Application No. 61/819,133, filed May 3, 2013, which are incorporated herein by reference in their entirety.

FIELD OF INVENTION

The present invention relates to methods and systems for the simultaneous production oxo-alcohols and products derived from oxo-alcohols.

BACKGROUND OF THE INVENTION

Presently, 2-ethylhexanol (2-EH) production processes begin with the hydroformylation of propylene to form a mixture of intermediate aldehydes, n-butanal (n-butyraldehyde) and isobutanal (isobutyraldehyde). The n-butanal stream is separated and then passed into an aldol condensation reactor to convert the n-butanal into 2 ethylpropyl acrolein (EPA), while the isobutanal is often burned off or removed as a by-product stream. The EPA stream is then passed to a hydrogenation reactor to form 2-ethylhexanol. On the other hand, the isobutanal stream may be hydrogenated in a separate hydrogenation reactor to produce isobutanol. Likewise, n-butanol producers hydrogenate the n-butanal stream in a separate hydrogenation reactor to produce n-butanol.

Accordingly, it would be beneficial to provide an integrated process and system that can utilize one hydrogenation reactor to simultaneously produce n-butanol, isobutanol, and 2-EH, and thereby maximize utilization of equipment and minimize capital expenditure. Additionally, it would also be beneficial to provide methods and systems that are able to use low value, by-product streams to produce high value products. These and other advantages are provided by various aspects of the present disclosure.

SUMMARY OF THE INVENTION

In accordance with the purpose(s) of the present invention, as embodied and broadly described herein, in one aspect, the invention relates to a method for the simultaneous production of oxo-alcohols, the method comprising: providing a propylene stream and a syngas stream; hydroformylating the propylene stream and syngas stream to provide a first aldehyde stream comprising n-butanal (NBAL) and isobutanal (IBAL); aldolizing at least a portion of the NBAL to provide a second aldehyde stream comprising 2-ethylhexenal (EPA); and hydrogenating simultaneously at least a portion of the first aldehyde stream and the second aldehyde stream to provide an alcohol stream comprising n-butanol, isobutanol, and 2-ethylhexanol; wherein hydrogenating step is performed in a single hydrogenation reactor.

In another aspect, the invention relates to a method for the simultaneous production of oxo-alcohols and plasticizers, the method comprising: providing a propylene stream and a syngas stream; hydroformylating the propylene stream and syngas stream to provide a first aldehyde stream comprising n-butanal (NBAL) and isobutanal (IBAL); aldolizing at least a portion of the NBAL to provide a second aldehyde stream comprising 2 ethylhexenal (EPA); hydrogenating simultaneously at least a portion of the first aldehyde stream and the second aldehyde stream to provide an alcohol stream comprising n-butanol, isobutanol, and 2-ethylhexanol, wherein the hydrogenating step is performed in a single hydrogenation reactor; and esterifying the alcohol stream with phthalic acid or anhydride to produce a phthalate stream comprising dibutyl phthalate, diisobutyl phthalate, and di-(2-ethylhexyl) phthalate.

In another aspect, the invention relates to a method for the simultaneous production of oxo-alcohols and plasticizers, the method comprising: providing a propylene stream and a syngas stream; hydroformylating the propylene stream and syngas stream to provide a first aldehyde stream comprising n-butanal (NBAL) and isobutanal (IBAL); aldolizing at least a portion of the NBAL to provide a second aldehyde stream comprising 2 ethylhexenal (EPA); aldolizing at least a portion of the IBAL with formaldehyde (FA) to provide a third aldehyde stream comprising hydroxypivaldehyde (HPA); hydrogenating simultaneously at least a portion of the first aldehyde stream, the second aldehyde stream, and the third aldehyde stream to provide an alcohol stream comprising n-butanol, isobutanol, and 2-ethylhexanol and a glycol stream comprising neopentylglycol; wherein the hydrogenation step is performed in a single hydrogenation reactor; and esterifying the alcohol stream with phthalic acid or anhydride to produce a phthalate stream comprising dibutyl phthalate, diisobutyl phthalate, and di-(2-ethylhexyl) phthalate.

In another aspect, the invention relates to a system for the simultaneous production of oxo-alcohols, the system comprising: an aldehyde production unit configured to receive a propylene feed and a syngas feed and configured to provide a first aldehyde stream comprising n-butanal (NBAL) and isobutanal (IBAL); an aldol condensation unit configured to receive at least a portion of the NBAL provided by the aldehyde production unit and configured to provide a second aldehyde stream comprising 2-ethyl hexanal (EPA); and an alcohol production unit configured to receive the first and the second aldehyde streams and configured to provide an alcohol stream comprising n-butanol, isobutanol, and 2-ethylhexanol.

In another aspect, the invention relates to a system for the simultaneous production of oxo-alcohols and plasticizers, the system comprising: an aldehyde production unit configured to receive a propylene feed and a syngas feed and configured to provide a first aldehyde stream comprising n-butanal (NBAL) and isobutanal (IBAL); an aldol condensation unit configured to receive at least a portion of the NBAL provided by the aldehyde production unit and configured to provide a second aldehyde stream comprising 2-ethyl hexanal (EPA); an alcohol production unit configured to receive the first and the second aldehyde streams and configured to provide an alcohol stream comprising n-butanol, isobutanol, and 2-ethylhexanol; and a phthalate production unit configured to receive the alcohol stream and configured to provide a phthalate stream comprising dibutyl phthalate, diisobutyl phthalate, and di-(2-ethylhexyl) phthalate.

In another aspect, the invention relates a system for the simultaneous production of oxo-alcohols and plasticizers, the system comprising: an aldehyde production unit configured to receive a propylene feed and a syngas feed and configured to provide a first aldehyde stream comprising n-butanal (NBAL) and isobutanal (IBAL); an first aldol condensation unit configured to receive at least a portion of the NBAL provided by the aldehyde production unit and configured to provide a second aldehyde stream comprising 2-ethyl hexanal (EPA); an second aldol condensation unit configured to receive at least a portion of the IBAL provided by the aldehyde production unit and configured to provide a third aldehyde stream comprising hydroxypivaldehyde; an alcohol production unit configured to receive the first, the second, and third aldehyde streams and configured to provide an alcohol stream comprising n-butanol, isobutanol, and 2-ethylhexanol, and a glycol stream comprising neopentylglycol; and a phthalate production unit configured to receive the alcohol stream and configured to provide a phthalate stream comprising dibutyl phthalate, diisobutyl phthalate, and di-(2-ethylhexyl) phthalate.

In various further aspects, the disclosed methods and systems provide several economical and operational advantages. In one aspect, the methods and systems utilize low-value, by-product streams to produce high-value product streams. In a further aspect, the disclosed methods and systems also provide improved production flexibility for a plant. In a still further aspect, the disclosed methods and systems also exhibit improve site efficiencies over plants of the prior art.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects and together with the description, serve to explain the principles of the compositions, methods and systems disclosed herein.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

Definitions

It is also to be understood that the terminology used herein is for the purpose of describing particular aspects only and is not intended to be limiting. As used in the specification and in the claims, the term "comprising" can include the embodiments "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "an alcohol stream" includes mixtures of two or more alcohol streams.

As used herein, the term "combination" is inclusive of blends, mixtures, alloys, reaction products, and the like.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

Disclosed are the components to be used to prepare the methods and systems of the invention as well as the compositions to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

References in the specification and concluding claims to parts by weight (pbw), of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this invention belongs.

As used herein the terms "weight percent," "wt %," and "wt. %," which can be used interchangeably, indicate the percent by weight of a given component based on the total weight of the composition, unless otherwise specified. That is, unless otherwise specified, all weight percent values are based on the total weight of the composition. It should be understood that the sum of weight percent values for all components in a disclosed composition or formulation are equal to 100.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

Methods for Simultaneous Production of Oxo-Alcohols and Plasticizers

As briefly described above, the present disclosure relates, in one aspect, to methods for the simultaneous production of oxo-alcohols. In further aspects, the invention relates to methods for the simultaneous production of oxo-alcohols and plasticizers. In various further aspects, the invention relates methods for the simultaneous production of oxo-alcohols and plasticizers wherein one catalytic reactor is needed for hydrogenation reactions and one catalytic reactor is needed for the esterification reactions. In still further aspects, the methods utilize low-value mixed aldehyde streams and mixed alcohol streams to produce high-value products.

In a further aspect, described herein are methods for the simultaneous production of oxo-alcohols, the method comprising: providing a propylene stream and a syngas stream; hydroformylating the propylene stream and syngas stream to produce a first aldehyde stream comprising n-butanal (NBAL) and isobutanal (IBAL); aldolizing at least a portion of the NBAL to produce a second aldehyde stream comprising 2 ethylhexenal (EPA); and hydrogenating simultaneously at least a portion of the first aldehyde stream and the second aldehyde stream to produce an alcohol stream comprising n-butanol, isobutanol, and 2-ethylhexanol; wherein the hydrogenation step is performed in a single hydrogenation reactor.

In another aspect, described herein are methods for the simultaneous production of oxo-alcohols and plasticizers, the method comprising: providing a propylene stream and a syngas stream; hydroformylating the propylene stream and syngas stream to produce a first aldehyde stream comprising n-butanal (NBAL) and isobutanal (IBAL); aldolizing at least a portion of the NBAL to produce a second aldehyde stream comprising 2 ethylhexenal (EPA); hydrogenating simultaneously at least a portion of the first aldehyde stream and the second aldehyde stream to produce an alcohol stream comprising n-butanol, isobutanol, and 2-ethylhexanol, wherein the hydrogenation step is performed in a single hydrogenation reactor; and esterifying the alcohol stream with phthalic acid or anhydride to produce a phthalate stream comprising dibutyl phthalate, diisobutyl phthalate, and di-(2-ethylhexyl) phthalate.

In another aspect, described herein are methods for the simultaneous production of oxo-alcohols and plasticizers, the method comprising: providing a propylene stream and a syngas stream; hydroformylating the propylene stream and syngas stream to produce a first aldehyde stream comprising n-butanal (NBAL) and isobutanal (IBAL); aldolizing at least a portion of the NBAL to produce a second aldehyde stream comprising 2 ethylhexenal (EPA); aldolizing at least a portion of the IBAL with Formaldehyde (FA) to produce a third aldehyde stream comprising hydroxypivaldehyde; hydrogenating simultaneously at least a portion of the first aldehyde stream, the second aldehyde stream, and the third aldehyde stream to produce an alcohol stream comprising n-butanol, isobutanol, and 2-ethylhexanol and a glycol stream comprising neopentylglycol, wherein the hydrogenation step is performed in a single hydrogenation reactor; and esterifying the alcohol stream with phthalic acid or anhydride to produce a phthalate stream comprising dibutyl phthalate, diisobutyl phthalate, and di-(2-ethylhexyl) phthalate.

In some aspects, the method comprises hydroformylating a propylene stream and a syngas stream to provide an aldehyde stream. In a further aspect, the propylene stream and a syngas stream is hydroformylated to produce an aldehyde stream comprising n-butanal (NBAL) and isobutanal (IBAL).

In a further aspect, the hydroformylation is performed in the presence of a catalyst. In a still further aspect, the catalyst comprises a hydroformylation catalyst. In a yet further aspect, the catalyst comprises any suitable hydroformylation catalysts capable of converting a propylene stream and a syngas stream to produce an aldehyde stream. Non-limiting examples of suitable hydroformylation catalyst include Cobalt or Rhodium based catalysts. In an exemplary aspect, the hydroformylation catalyst comprises tri-phenylphosphine modified Rhodium catalyst.

In various aspects, the methods comprises separating at least a portion of a product stream, for example, a mixed product stream comprising more than one compound. In a further aspect, the method comprise separating at least a portion of an aldehyde stream. In a still further aspect, an aldehyde stream comprising NBAL and IBAL is separated to provide a NBAL stream and an IBAL stream. In a yet further aspect, the separation step is performed by any suitable means capable of separating a mixed aldehyde stream into discrete aldehyde streams. Non-limiting examples of methods of separating include distillation, extraction, decanting, preferably by using at least one distillation columns.

In various aspects, the present methods produce an alcohol stream when provided with an aldehyde stream. In other aspects, the present methods are configured to utilize aldehyde streams of varying composition and compositional ratio. In further aspects, the aldehyde stream composition and compositional ratio can be selected to produce any desired amount of a disclosed alcohol. For example, according to still further aspects, the composition and compositional ratio of the alcohol stream is controlled by adjusting the ratio of the corresponding aldehyde in the aldehyde stream.

In further aspects, the present methods can also utilize aldehyde streams having any composition and compositional ratio based on plant production availability of a given aldehyde. That is, in still further aspects, the manufacturing parameters and conditions can be selected to maximize overall yields rather than selecting parameters and conditions for the sole purpose of minimizing undesired aldehydes.

In one aspect, the aldehyde stream comprises a first aldehyde stream, a second aldehyde stream, or a third aldehyde stream, or combinations thereof. In another aspect, the aldehyde stream is a mixed aldehyde stream comprising more than one of a first aldehyde stream, a second aldehyde stream, and a third aldehyde stream, for example, a mixed aldehyde stream comprising a first aldehyde stream and a second aldehyde stream.

In a further aspect, the aldehyde stream comprises a first aldehyde stream comprising at least one of NBAL and IBAL. In a still further aspect, the first aldehyde stream comprises NBAL and IBAL. In a yet further aspect, the first aldehyde stream comprises from 0 to 100 weight % NBAL and from 0 to 100 weight % IBAL. For example, according to aspects of the disclosure, the NBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the NBAL can be present within any range of amount derived from any two of the above stated values. For example, the NBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the IBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the IBAL can be present within any range of amount derived from any two of the above stated values. For example, the IBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In another aspect, the aldehyde stream comprises a first aldehyde stream comprising at least one of NBAL and IBAL, and a second aldehyde stream comprising EPA. In a further aspect, the aldehyde stream comprises from 0 to 100 wt % NBAL, from 0 to 100 wt % IBAL, and from 0 to 100 wt % EPA. For example, according to aspects of the disclosure, the NBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the NBAL can be present within any range of amount derived from any two of the above stated values. For example, the NBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the IBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the IBAL can be present within any range of amount derived from any two of the above stated values. For example, the IBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the EPA can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the EPA can be present within any range of amount derived from any two of the above stated values. For example, the EPA can be present in an amount in the range of from 5 to 15 weight %, or in an amount in the range of from 5 weight % to 20 weight %, or in an amount in the range of from 50 weight % to 85 weight % relative to the total weight of the aldehyde stream.

In another aspect, the aldehyde stream comprises a third aldehyde stream comprising hydroxypivaldehyde. In a further aspect, the aldehyde stream comprises from 0 to 100 wt % hydroxypivaldehyde. For example, according to aspects of the disclosure, the hydroxypivaldehyde can be present in an amount in the range of from 0 weight % up to 100 weight % relative to the total weight of the third aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the hydroxypivaldehyde can be present within any range of amount derived from any two of the above stated values. For example, the hydroxypivaldehyde can be present in an amount in the range of from 5 to 15 weight %, or in an amount in the range of from 5 weight % to 20 weight %, or in an amount in the range of from 50 weight % to 85 weight % relative to the total weight of the aldehyde stream.

According to various aspects, the methods also comprise at least one aldolization step. In some aspects, a NBAL stream is aldolized to produce a second aldehyde stream. In further aspects, the second aldehyde stream comprises EPA.

In other aspects, the methods comprise aldolizing at least a portion of an IBAL stream to produce a third aldehyde stream comprising hydroxypivaldehyde.

In various further aspects, the aldolization step is performed in the presence of a catalyst. In one aspect, the aldolization step is performed in the presence of a condensation catalyst. Non-limiting examples of suitable condensation catalysts include alkali hydroxides, alkali carbonates, alkaline earth metal hydroxide. Other suitable catalyst systems include Zn or Mg containing zeolites, tertiary amines and basic ion exchange resins. In an exemplary aspects, the condensation catalyst comprise a tertiary amine catalyst.

In another aspect, the aldolization step is performed in the presence of an amine catalyst. Non-limiting examples of suitable amine catalysts include triethylenediamine (TEDA), 1,4-diazabicyclo[2.2.2]octane (DABCO) and dimethylcyclohexylamine (DMCHA), preferably triethyl amine (TEA).

According to other aspects of invention, the one or more aldehyde streams are hydrogenated simultaneously to produce an alcohol stream. That is, according to further aspects, the present methods utilize a single catalytic reactor for hydrogenation reactions.

In further aspects, the hydrogenation reaction is performed in the presence of a hydrogenation catalyst. Non-limiting examples of suitable hydrogenation catalyst include Raney nickel, Ni—Cr, Cu—Zn, Cu—Al, Cu—Cr and Cr—Ba. In an exemplary aspect, the hydrogenation catalyst comprises CuO/ZnO catalyst in the presence of aluminum.

In further aspects, the disclosed methods can be configured to produce or utilize alcohol streams of any varying composition and compositional ratio. In one aspect, the composition and compositional ratio of the aldehyde stream can be controlled to produce any desired amount of a disclosed alcohol. In still further aspects, the composition and compositional ratio of the alcohol stream is controlled by adjusting the ratio of the corresponding aldehyde in the aldehyde stream.

In one aspect, the aldehyde stream is hydrogenated to produce an alcohol stream comprising butanol, isobutanol, or 2-ethylhexanol, or combinations thereof. In a further aspect, the alcohol stream comprises butanol, isobutanol, and 2-ethylhexanol.

In a further aspect, the alcohol stream comprises from 0 to 100 weight % butanol, from 0 to 100 weight % isobutanol, and from 0 to 100 weight % 2-ethylhexanol. For example, according to aspects of the disclosure, the butanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the butanol can be present within any range of amount derived from any two of the above stated values. For example, the butanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, the isobutanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the isobutanol can be present within any range of amount derived from any two of the above stated values. For example, the isobutanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, the 2-ethylhexanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the 2-ethylhexanol can be present within any range of amount derived from any two of the above states values. For example, the 2-ethylhexanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, at least a portion of the third aldehyde stream comprising hydroxypivaldehyde is hydrogenated to produce a glycol stream. In a still further aspect, the third aldehyde stream comprising hydroxypivaldehyde is hydrogenated simultaneously to produce a glycol stream. In other aspects, the third aldehyde stream comprising hydroxypivaldehyde is hydrogenated in a separate reactor to produce a glycol stream. In still further aspect, the glycol stream comprises neopentylglycol (NPG). In yet further aspects, neopentylglycol (NPG) is produced by condensation of isobutyraldehyde with Formaldehyde (FA) in the presence of a phase transfer catalyst (PTC).

In a further aspect, the alcohol stream is subjected to a separation step. In a yet further aspect, at least a portion of the alcohol stream is separated into at least one of a butanol stream, an isobutanol stream, or a 2-ethylhexanol stream.

According to further aspects of the invention, the alcohol stream is esterified to produce a phthalate stream. In still further aspects, the method comprises esterifying the alcohol stream with phthalic acid or anhydride to produce a phthalate stream comprising dibutyl phthalate, diisobutyl phthalate, and di-(2-ethylhexyl) phthalate.

In a further aspect, a single catalytic reactor is used to perform esterification reactions. In a still further aspect, the esterification reaction is performed in the presence of a esterification catalyst. Non-limiting examples of suitable esterification catalyst include strong acids, amine based catalyst such as 4-dimethylaminopyridine (DMAP), and antimony based catalyst antimony triacetate. In an exemplary aspect, the esterification catalyst comprises tetraisoproypl titanate.

In a further aspect, the composition and compositional ratio of the phthalate stream can be controlled to produce any amount of a disclosed phthalate. In a still further aspect, the composition and compositional ratio of the phthalate stream is controlled by adjusting the ratio of the corresponding alcohol in the alcohol stream.

That is, in one aspect, the phthalate stream comprises dibutyl phthalate, diisobutyl phthalate, or di-(2-ethylhexyl) phthalate, or combinations thereof. In a further aspect, the phthalate stream comprises dibutyl phthalate, diisobutyl phthalate, and di-(2-ethylhexyl) phthalate.

In another aspect, the phthalate stream comprises from 0 to 100 weight % dibutyl phthalate, from 0 to 100 weight % diisobutyl phthalate, and from 0 to 100 weight % di-(2-ethylhexyl) phthalate. For example, according to aspects of the disclosure, the dibutyl phthalate can be present in an amount in the range of from 0 weight % up to 100 weight % relative to the total weight of the phthalate stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the dibutyl phthalate can be present within any range of amount derived from any two of the above stated values. For example, the dibutyl phthalate can be present in an amount in the range of from 5 to 15 weight %, or in an amount in the range of from 5 weight % to 20 weight %, or in an amount in the range of from 50 weight % to 85 weight % relative to the total weight of the phthalate stream.

In a further aspect, the diisobutyl phthalate can be present in an amount in the range of from 0 weight % up to 100 weight % relative to the total weight of the phthalate stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the diisobutyl phthalate can be present within any range of amount derived from any two of the above stated values. For example, the diisobutyl phthalate can be present in an amount in the range of from 5 to 15 weight %, or in an amount in the range of from 5 weight % to 20 weight %, or in an amount in the range of from 50 weight % to 85 weight % relative to the total weight of the phthalate stream.

In a further aspect, the di-(2-ethylhexyl) phthalate can be present in an amount in the range of from 0 weight % up to 100 weight % relative to the total weight of the phthalate stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the di-(2-ethylhexyl) phthalate can be present within any range of amount derived from any two of the above stated values. For example, the di-(2-ethylhexyl) phthalate can be present in an amount in the range of from 5 to 15 weight %, or in an amount in the range of from 5 weight % to 20 weight %, or in an amount in the range of from 50 weight % to 85 weight % relative to the total weight of the phthalate stream.

In a further aspect, the phthalate stream is subjected to a separation step. In a yet further aspect, at least a portion of the phthalate stream is separated into at least one of a dibutyl phthalate stream, a diisobutyl phthalate stream, or a di-(2-ethylhexyl) phthalate stream.

Systems for Simultaneous Production of Oxo-Alcohols and Plasticizers

In one aspect, the present disclosure also relates to a system for the simultaneous production of oxo-alcohols, the system comprising: an aldehyde production unit configured to receive a propylene feed and a syngas feed and configured to produce a first aldehyde stream comprising n-butanal (NBAL) and isobutanal (IBAL); an aldol condensation unit configured to receive at least a portion of the NBAL produced by the aldehyde production unit and configured to produce a second aldehyde stream comprising 2-ethyl hexanal (EPA); and an alcohol production unit configured to receive the first and the second aldehyde streams and configured to produce an alcohol stream comprising n-butanol, isobutanol, and 2-ethylhexanol.

In a further aspect, disclosed is a system for the simultaneous production of oxo-alcohols and plasticizers, the system comprising: an aldehyde production unit configured to receive a propylene feed and a syngas feed and configured to produce a first aldehyde stream comprising n-butanal (NBAL) and isobutanal (IBAL); an aldol condensation unit configured to receive at least a portion of the NBAL produced by the aldehyde production unit and configured to produce a second aldehyde stream comprising 2-ethyl hexanal (EPA); an alcohol production unit configured to receive the first and the second aldehyde streams and configured to produce an alcohol stream comprising n-butanol, isobutanol, and 2-ethylhexanol; and a phthalate production unit configured to receive the alcohol stream and configured to produce a phthalate stream comprising dibutyl phthalate, diisobutyl phthalate, and di-(2-ethylhexyl) phthalate.

In a further aspect, disclosed is a system for the simultaneous production of oxo-alcohols and plasticizers, the system comprising: an aldehyde production unit configured to receive a propylene feed and a syngas feed and configured to produce a first aldehyde stream comprising n-butanal (NBAL) and isobutanal (IBAL); an first aldol condensation unit configured to receive at least a portion of the NBAL produced by the aldehyde production unit and configured to produce a second aldehyde stream comprising 2-ethyl hexanal (EPA); an second aldol condensation unit configured to receive at least a portion of the IBAL produced by the aldehyde production unit and configured to produce a third aldehyde stream comprising hydroxypivaldehyde; an alcohol production unit configured to receive the first, the second, and third aldehyde streams and configured to produce an alcohol stream comprising n-butanol, isobutanol, and 2-ethylhexanol, and a glycol stream comprising neopentylglycol; and a phthalate production unit configured to receive the alcohol stream and configured to produce a phthalate stream comprising dibutyl phthalate, diisobutyl phthalate, and di-(2-ethylhexyl) phthalate.

In one aspect, the aldehyde production unit comprises a hydroformylation subunit. In a still further aspect, the hydroformylation subunit comprises a fixed bed reactor, moving bed reactor, fluid bed reactor, stirred tank reactor, plug flow reactor, or distillation column reactors. In some aspects, the aldehyde production unit comprises a stirred tank reactor.

In a further aspect, the aldehyde production unit comprises a hydroformylation catalyst. In still further aspects, hydroformylation catalyst comprises Cobalt or Rhodium based catalysts. In an exemplary aspect, the hydroformylation catalyst comprises tri-phenylphosphine modified Rhodium catalyst.

In a further aspect, the hydroformylation subunit is configured to convert propylene and syngas into an aldehyde stream. In a still further aspect, the aldehyde stream comprises a first aldehyde stream comprising NBAL and IBAL.

In various aspects, the methods comprise at least one separation unit. In some aspects, the separation unit is configured to separate at least a portion of a product stream, for example, a mixed product stream comprising more than one compound. In a further aspect, the system comprises an aldehyde separation unit. In a still further aspect, the aldehyde separation unit is configured to receive a mixed aldehyde stream and configured to provide discrete aldehyde streams. In a yet further aspect, the aldehyde separation unit is configured to receive the first aldehyde stream and configured to produce a n-butanal stream and an isobutanal stream.

In a further aspect, the system comprises at least one aldol condensation unit. In a still further aspect, the aldol condensation unit is configured to receive at least a portion of a NBAL stream produced by the aldehyde production unit and configured to produce a second aldehyde stream comprising 2-ethyl hexanal (EPA). In a still further aspect, the aldol condensation unit comprises a condensation catalyst. Non-limiting examples of suitable condensation catalysts include triethylenediamine (TEDA), 1,4-diazabicyclo[2.2.2] octane (DABCO) and dimethylcyclohexylamine (DMCHA), triethyl amine (TEA), and a combination thereof. In exemplary aspects, the condensation catalyst comprises triethyl amine (TEA).

In a further aspect, the aldol condensation unit is configured to receive a formaldehyde stream and at least a portion of a IBAL stream produced by the aldehyde production unit and configured to produce a third aldehyde stream comprising hydroxypivaldehyde. In a still further aspect, the aldol condensation unit comprises a PTC catalyst. Non-limiting examples of suitable PTC catalysts include triethyl amine (TEA).

In various aspects, the system comprises an alcohol production unit. In a further aspect, the alcohol production unit comprises a hydrogenation subunit. In a still further aspect, the hydrogenation subunit comprises a fixed bed reactor, moving bed reactor, fluid bed reactor, stirred tank reactor, plug flow reactor, distillation column reactors, or a combination thereof. In exemplary aspects, the hydrogenation subunit comprises a fixed bed reactor.

In a yet further aspect, the hydrogenation subunit is a fixed bed reactor. In a still further aspect, the alcohol production unit comprises a hydrogenation catalyst. In still further aspects, the hydrogenation catalyst comprises Raney nickel, Ni—Cr, Cu—Zn, Cu—Al, Cu—Cr and Cr—Ba. In exemplary aspects, the hydrogenation catalyst comprises CuO/ZnO catalyst in the presence of aluminum.

In various further aspects, the hydrogenation subunit is configured to convert at least one aldehyde stream into an alcohol stream. In one aspect, the aldehyde stream comprises a first aldehyde stream, a second aldehyde stream, or a third aldehyde stream, or combinations thereof. In another aspect, the aldehyde stream is a mixed aldehyde stream comprising more that one of a first aldehyde stream, a second aldehyde stream, and a third aldehyde stream, for example, a mixed aldehyde stream comprising a first aldehyde stream and a second aldehyde stream.

In some aspects, the aldehyde stream comprises a first aldehyde stream comprising at least one of NBAL and IBAL. In a further aspect, the first aldehyde stream comprises NBAL and IBAL. In a yet further aspect, the first aldehyde stream comprises from 0 to 100 weight % NBAL and from 0 to 100 weight % IBAL. For example, according to aspects of the disclosure, the NBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the NBAL can be present within any range of amount derived from any two of the above stated values. For example, the NBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the IBAL can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the IBAL can be present within any range of amount derived from any two of the above stated values. For example, the IBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In another aspect, the aldehyde stream comprises a first aldehyde stream comprising at least one of NBAL and IBAL, and a second aldehyde stream comprising EPA. In a further aspect, the aldehyde stream comprises from 0 to 100 wt % NBAL, from 0 to 100 wt % IBAL, and from 0 to 100 wt % EPA. For example, according to aspects of the disclosure, the NBAL can be present in an amount in the range of from 0 weight % up to 100 weight % relative to the total weight of the mixed aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the NBAL can be present within any range of amount derived from any two of the above stated values. For example, the NBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the IBAL can be present in an amount in the range of from 0 weight % up to 100 weight % relative to the total weight of the mixed aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the IBAL can be present within any range of amount derived from any two of the above stated values. For example, the IBAL can be present in an amount in the range of from 5 to 15 weight %, or in an amount in the range of from 5 weight % to 20 weight %, or in an amount in the range of from 50 weight % to 85 weight % relative to the total weight of the aldehyde stream.

In a further aspect, the EPA can be present in an amount in the range of from 0 weight % up to 100 weight % relative to the total weight of the mixed aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the EPA can be present within any range of amount derived from any two of the above stated values. For example, the EPA can be present in an amount in the range of from 5 to 15 weight %, or in an amount in the range of from 5 weight % to 20 weight %, or in an amount in the range of from 50 weight % to 85 weight % relative to the total weight of the aldehyde stream.

In another aspect, the aldehyde stream comprises a third aldehyde stream comprising hydroxypivaldehyde. In a further aspect, the aldehyde stream comprises from 0 to 100 wt % hydroxypivaldehyde. For example, according to aspects of the disclosure, the hydroxypivaldehyde can be present in an amount in the range of from 0 weight % up to 100 weight % relative to the total weight of the aldehyde stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the hydroxypivaldehyde can be present within any range of amount derived from any two of the above stated values. For example, the hydroxypivaldehyde can be present in an amount in the range of from 5 to 15 weight %, or in an amount in the range of from 5 weight % to 20 weight %, or in an amount in the range of from 50 weight % to 85 weight % relative to the total weight of the aldehyde stream.

In various further aspects, the system also includes a phthalate production unit. In a further aspect, the phthalate production unit comprises an esterification subunit. In a further aspect, the esterification subunit comprises a catalytic reactor. In a still further aspect, the catalytic reactor comprises conventional stirrered tank reactors (CSTR).

In a further aspect, the esterification subunit comprises an esterification catalyst. In still further aspects, the esterification catalyst comprises tetraisoproypl titanate catalyst.

According to some aspects, the esterification subunit is configured to receive an alcohol stream and configured to produce a phthalate stream. In a further aspect, the esterification unit is configured to receive an alcohol stream produced by the alcohol production unit and configured to produce a phthalate stream comprising dibutyl phthalate, diisobutyl phthalate, and di-(2-ethylhexyl) phthalate.

In various aspects, the present systems can produce and utilize alcohol streams of varying composition or compositional ratio. For example, in one aspect, the alcohol stream comprises butanol, isobutanol, or 2-ethylhexanol, or combinations thereof. In another aspect, the alcohol stream comprises butanol, isobutanol, and 2-ethylhexanol.

Thus, in further aspects, the alcohol stream comprises from 0 to 100 weight % butanol, from 0 to 100 weight % isobutanol, and from 0 to 100 weight % 2-ethylhexanol. For example, according to aspects of the disclosure, the butanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the butanol can be present within any range of amount derived from any two of the above stated values. For example, the butanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, the isobutanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the isobutanol can be present within any range of amount derived from any two of the above stated values. For example, the isobutanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, the 2-ethylhexanol can be present in an amount in the range of from 0 weight % up to 100 weight % relative to the total weight of the alcohol stream, including further exemplary amounts of 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, 95 weight %. In still further aspects, the 2-ethylhexanol can be present within any range of amount derived from any two of the above states values. For example, the 2-ethylhexanol can be present in an amount in the range of from 5 to 15 weight %, or in an amount in the range of from 5 weight % to 20 weight %, or in an amount in the range of from 50 weight % to 85 weight % relative to the total weight of the alcohol stream.

In a further aspect, the system comprises a phthalate separation unit. In a still further aspect, the phthalate separation unit is configured to receive a mixed phthalate stream and configured to provide discrete phthalate streams. For example, in a yet further aspect, the phthalate separation unit is configured to receive a mixed phthalate stream and configured to produce a dibutyl phthalate stream, a diisobutyl phthalate stream, and a di-(2-ethylhexyl) phthalate stream.

In various aspects, the disclosed methods and systems provide several economical and operational advantages. In one aspect, the methods and systems utilize low-value, by-product streams to produce high-value product streams. For example, mixtures of aldehydes and alcohols are generally considered low-value streams and commonly used as fuel. In another aspect, the method and systems of the present invention simultaneously produce oxo-alcohols from an aldehyde stream including mixed aldehyde streams comprising NBAL, MAL, and EPA. In a further aspect, the methods and systems utilize alcohol streams including mixed alcohol streams to produce high-value plasticizer blends comprising a mixture of phthalates.

Since neither the aldehyde streams nor the alcohol streams require isolation or purification, the present methods and systems also provide improved production flexibility for a plant. That is, according to aspects of the disclosure, mixed product streams are produced and subsequently used downstream within the same plant without the added time and cost associated with purification and isolation. In further aspects, the various production and utilization stages each comprise a single catalytic reactor, thereby avoiding cost and upkeep associated with running separate catalytic reactors for individual products. In oen aspect, the n-butyraldehyde, isobutyraldehyde and 2-ethylpropyl acrolein (EPA) can be simultaneously using suitable metal catalysts because they have small carbon chains and are easier to hydrogenate. In other aspects, n-butyraldehyde is a primary aldehyde and isobutyraldehyde and 2-ethylpropyl acrolein are secondary aldehydes, therefore, their mixture are easier to hydrogenate simultaneously under suitable process conditions, in contrast to the tertiary aldehydes which are more difficult to hydrogenate.

In further aspect, because of the high-value utilization of by-product streams, the present methods and systems also have a reduced need for using highly selective catalysts that minimizes IBAL production. That is, according to further aspects, the present invention can employ lower cost catalysts because any IBAL produced is ultimately used in the production of a high-value product stream rather than being burned off as fuel. Thus, in still further aspects, the present invention allows manufacturing parameters and conditions to be selected to maximize overall product yields rather than selecting parameters and conditions for the sole purpose of minimizing low-value by-product streams.

In other aspects, the methods and systems of the present invention also exhibit improve site efficiencies over plants of the prior art. As described herein, only one catalytic reactor is needed for the hydrogenation reaction of aldehydes to their respective alcohols. In further aspects, only one catalytic reactor is needed for the esterification reaction of alcohols to their respective phthalates. Thus, by not requiring separate reactors, the present methods and systems also have the advantage of avoiding additional capital and maintenance expenses associated with multiple, separate reactors.

Figure 1:
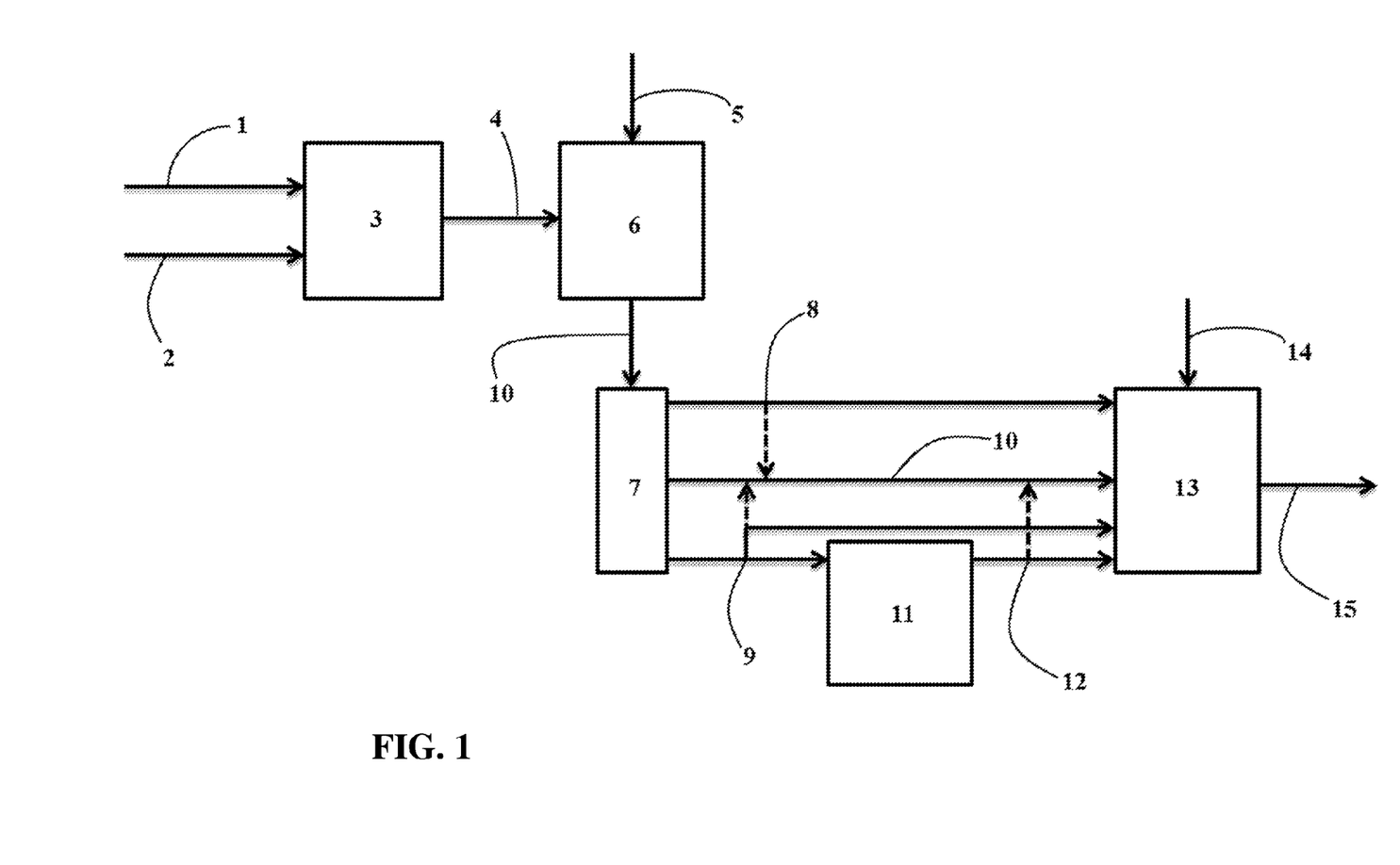
FIG. 1 shows a diagram illustrating an exemplary embodiment of the process for the production of oxo-alcohols in accordance with the present invention.

According to aspects of the disclosure, FIG. 1 shows an exemplary embodiment of a system employing the inventive processes. In one aspect, a natural gas feed 1 and steam 2 are provided to a syngas production unit 3 configured to receive a natural gas feed 1 and steam 2 and configured to produce a syngas stream 4. In a further aspect, the system comprises an aldehyde production unit 6 configured to receive a propylene feed 5 and the syngas stream 4 and configured to produce a first aldehyde stream 10. In a still further aspect, the first aldehyde stream 10 comprises n-butanal (NBAL) and isobutanal (IBAL).

In a further aspect, the system comprises an aldehyde separation unit 7. In a still further aspect, the aldehyde separation unit 7 is configured to separate at least a portion of the first aldehyde stream into a n-butanal (NBAL) stream 9 and an isobutanal (IBAL) stream 8.

In a further aspect, the system comprises an aldol condensation unit 11 configured to receive at least a portion of the NBAL 9 provided by the aldehyde production unit and configured to produce a second aldehyde stream 12 comprising 2-ethyl hexanal (EPA).

In a further aspect, the invention comprises an alcohol production unit 13 configured to receive at least one aldehyde stream 10 and a hydrogen stream 14, and configured to produce at least one alcohol stream 15. In a still further aspect, the alcohol production unit 13 is configured to receive the first aldehyde stream 10 and the second aldehyde stream 12 and configured to produce an alcohol stream 15 comprising n-butanol, isobutanol, and 2-ethylhexanol.

As described herein, the alcohol production unit 13 is configured to receive an aldehyde stream of varying composition, and configured to produce an alcohol stream 15 having any desired composition. In this aspect, at least one of the n-butanal (NBAL) stream 9, the isobutanal (IBAL) stream 8, and the second aldehyde stream 12 comprising 2-ethyl hexanal (EPA) can be optionally combined with the first aldehyde stream 10 prior to introduction into the alcohol production unit 13. In another aspect, the alcohol production unit 13 is configured to receive the n-butanal (NBAL) stream 9, the isobutanal (IBAL) stream 8, and the second aldehyde stream 12 comprising 2-ethyl hexanal (EPA). Thus, in a further aspect, the alcohol stream 15 comprises n-butanol, isobutanol, or 2-ethylhexanol, or combinations thereof.

Figure 2:
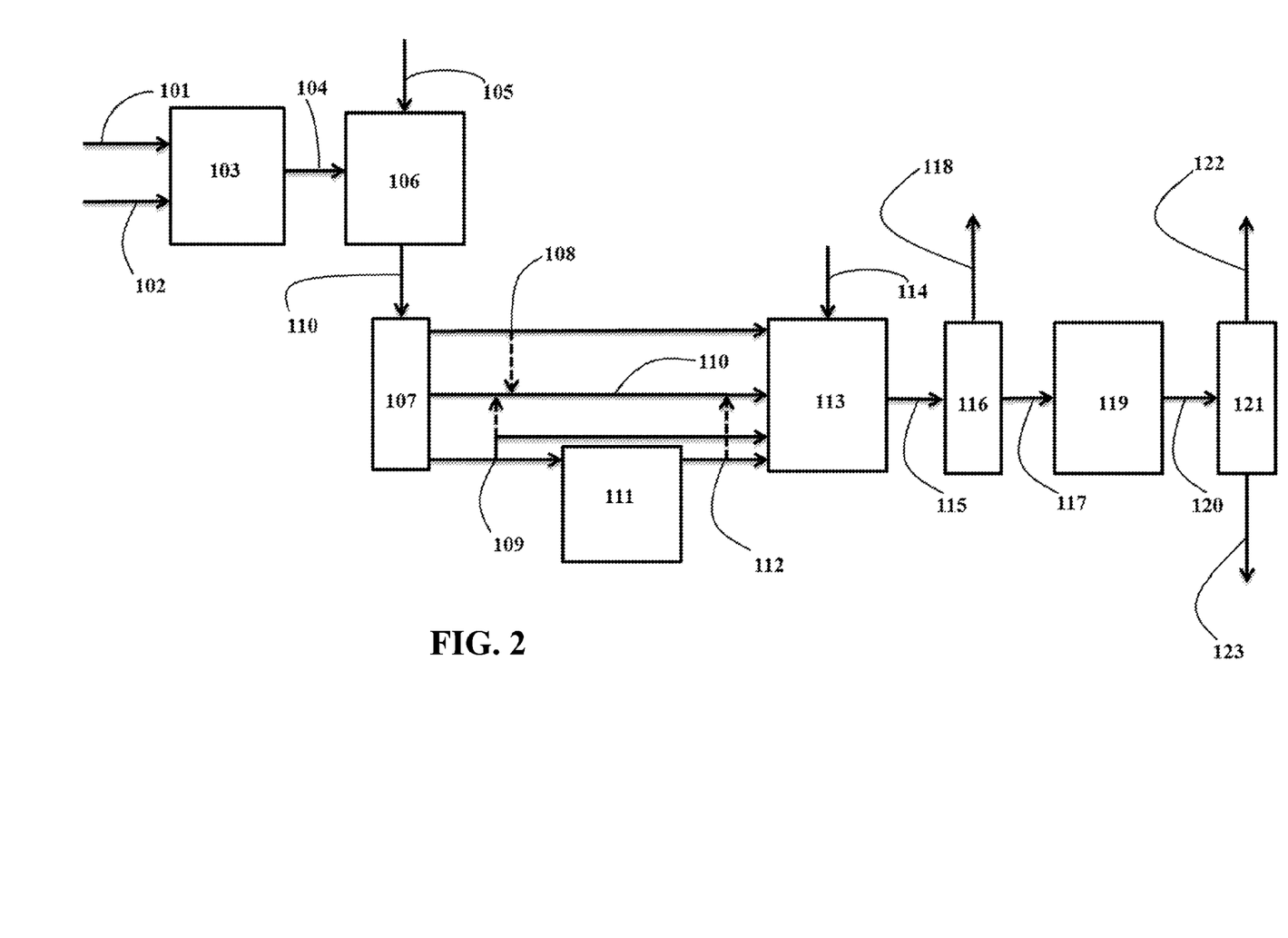
FIG. 2 shows a diagram illustrating an exemplary embodiment of the process for the production of oxo-alcohols and plasticizers in accordance with the present invention.

According to further aspects of the disclosure, FIG. 2 shows another exemplary embodiment of a system employing the inventive processes. In one aspect, a natural gas feed 101 and steam 102 are provided to a syngas production unit 103 configured to receive a natural gas feed 101 and steam 102 and configured to produce a syngas stream 104. In a further aspect, the system comprises an aldehyde production unit 106 configured to receive a propylene feed 105 and the syngas stream 104 and configured to produce a first aldehyde stream 110. In a still further aspect, the first aldehyde stream 110 comprises n-butanal (NBAL) and isobutanal (IBAL).

In a further aspect, the system comprises an aldehyde separation unit 107. In a still further aspect, the aldehyde separation unit 107 is configured to separate at least a portion of the first aldehyde stream into a n-butanal (NBAL) stream 109 and an isobutanal (IBAL) stream 108.

In a further aspect, the system comprises an aldol condensation unit 111 configured to receive at least a portion of the NBAL 109 provided by the aldehyde production unit and configured to produce a second aldehyde stream 112 comprising 2-ethyl hexanal (EPA).

In a further aspect, the system comprises an alcohol production unit 113 configured to receive at least one aldehyde stream 110 and a hydrogen stream 114, and configured to produce at least one alcohol stream 115. In a still further aspect, the alcohol production unit 113 is configured to receive the first aldehyde stream 110 and the second aldehyde stream 112 and configured to produce an alcohol stream 115 comprising n-butanol, isobutanol, and 2-ethylhexanol.

As described herein, the alcohol production unit 113 is configured to receive aldehyde streams of varying composition, and configured to produce an alcohol stream 115 having any desired composition. In this aspect, at least one of the n-butanal (NBAL) stream 109, the isobutanal (IBAL) stream 108, and the second aldehyde stream 112 comprising 2-ethyl hexanal (EPA) can be optionally combined with the first aldehyde stream 110 prior to introduction into the alcohol production unit 113. In another aspect, the alcohol production unit 113 is configured to receive the n-butanal (NBAL) stream 109, the isobutanal (IBAL) stream 108, and the second aldehyde stream 112 comprising 2-ethyl hexanal (EPA). Thus, in a further aspect, the alcohol stream 115 comprises n-butanol, isobutanol, or 2-ethylhexanol, or combinations thereof.

In a further aspect, the system comprises an alcohol separation unit 116. In a still further aspect, the alcohol separation unit 116 is configured to separate at least a portion of the alcohol stream 115 into a first alcohol substream 117 and a second alcohol substream 118. Depending on the composition of the alcohol stream 115 and desired downstream products, the first alcohol substream 117 and the second alcohol substream 118 will each comprise n-butanol, isobutanol, or 2-ethylhexanol, or combinations thereof.

In a further aspect, the system comprises a phthalate production unit 119 configured to receive at least one alcohol stream 117 and configured to produce a phthalate stream 120. As described herein, the phthalate production unit 119 is configured to receive alcohol streams of varying composition, and configured to produce a phthalate stream 120 having any desired composition. In one aspect, the phthalate production unit 119 is configured to receive an alcohol stream 117 comprising n-butanol, isobutanol, and 2-ethylhexanol and configured to produce a phthalate stream 120 comprising dibutyl phthalate, diisobutyl phthalate, and di-(2-ethylhexyl) phthalate. In a further aspect, the phthalate production unit 119 is configured to receive an alcohol stream 117 comprising n-butanol, isobutanol, or 2-ethylhexanol, or combinations thereof, and configured to produce a phthalate stream 120 comprising dibutyl phthalate, diisobutyl phthalate, or di-(2-ethylhexyl) phthalate, or combinations thereof.

In a further aspect, the system comprises an phthalate separation unit 121. In a still further aspect, the phthalate separation unit 121 is configured to separate at least a portion of the alcohol stream 120 into a first phthalate substream 122 and a second phthalate substream 123. Depending on the composition of the phthalate stream 115 and desired downstream products, the first phthalate substream 122 and the second phthalate substream 123 will each comprise dibutyl phthalate, diisobutyl phthalate, or di-(2-ethylhexyl) phthalate, or combinations thereof.

Figure 3:
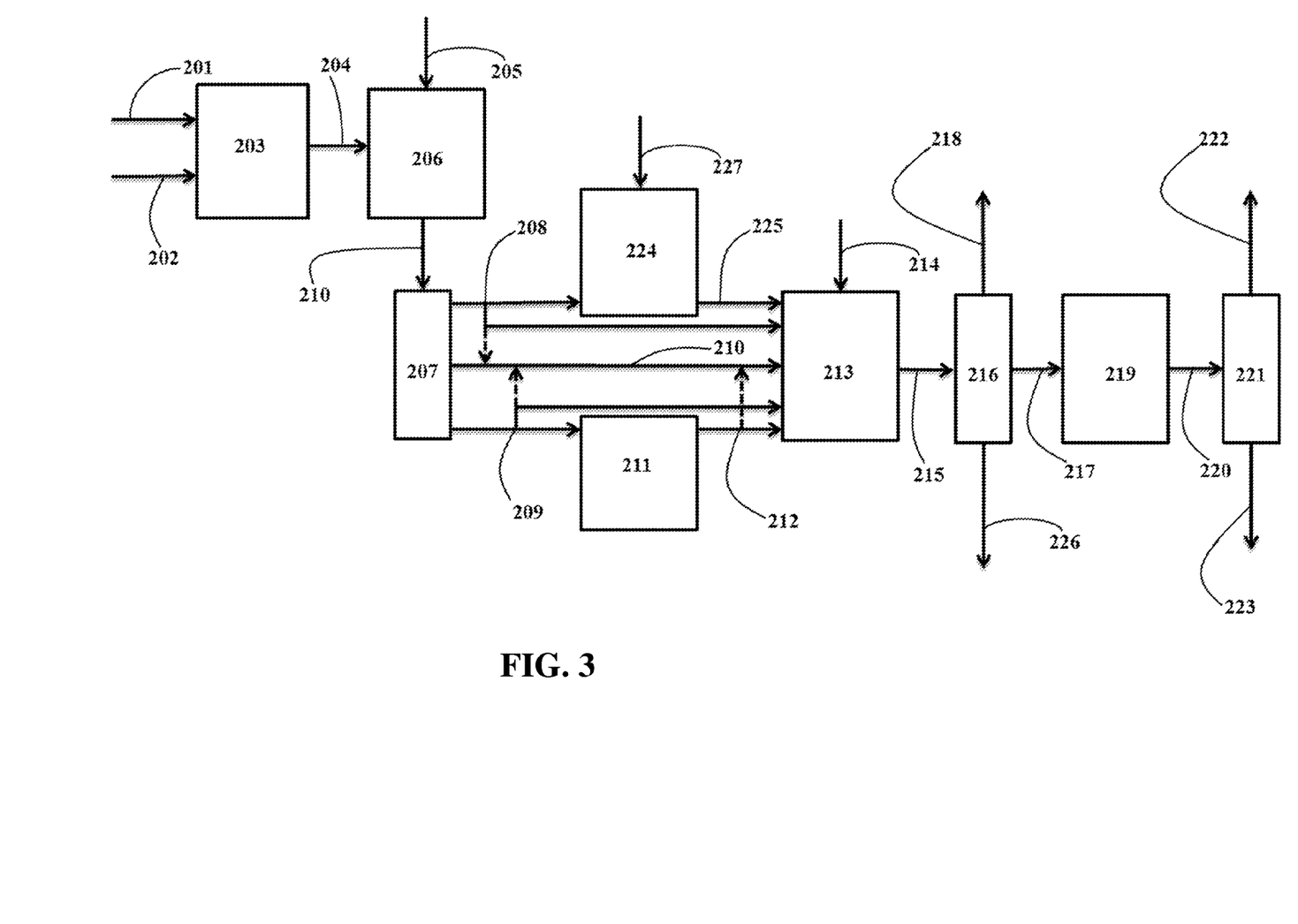
FIG. 3 shows a diagram illustrating an exemplary embodiment of the process production of oxo-alcohols and plasticizers in accordance with the present invention.

According to further aspects of the disclosure, FIG. 3 shows another exemplary embodiment of a system employing the inventive processes. In one aspect, a natural gas feed 201 and steam 202 are provided to a syngas production unit 203 configured to receive a natural gas feed 201 and steam 202 and configured to produce a syngas stream 204. In a further aspect, the system comprises an aldehyde production unit 206 configured to receive a propylene feed 205 and the syngas stream 204 and configured to produce a first aldehyde stream 210. In a still further aspect, the first aldehyde stream 210 comprises n-butanal (NBAL) and isobutanal (IBAL).

In a further aspect, the system comprises an aldehyde separation unit 207. In a still further aspect, the aldehyde separation unit 207 is configured to separate at least a portion of the first aldehyde stream into a n-butanal (NBAL) stream 209 and an isobutanal (IBAL) stream 208.

In a further aspect, the system comprises a first aldol condensation unit 211 and a second aldol condensation unit 224. In a still further aspect, the first aldol condensation unit 211 is configured to receive at least a portion of the NBAL 209 provided by the aldehyde production unit and configured to produce a second aldehyde stream 212 comprising 2-ethyl hexanal (EPA). In a yet further aspect, the second aldol condensation unit 211 configured to receive at least a portion of the IBAL 208 provided by the aldehyde production unit and and formaldehyde (FA) stream 227, and configured to produce a third aldehyde stream 225 comprising hydroxypivaldehyde.

In a further aspect, the system comprises an alcohol production unit 213 configured to receive at least one aldehyde stream 210 and a hydrogen stream 214, and configured to produce at least one alcohol stream 215. In a still further aspect, the alcohol production unit 213 is configured to receive the first aldehyde stream 210 and the second aldehyde stream 212 and configured to produce an alcohol stream 215 comprising n-butanol, isobutanol, and 2-ethylhexanol. In a yet further aspect, the alcohol production unit 213 is configured to receive the first aldehyde stream 210, the second aldehyde stream 212, and the third aldehyde stream 227, and configured to produce an alcohol stream 215 comprising n-butanol, isobutanol, 2-ethylhexanol, and neopentylglycol.

As described herein, the alcohol production unit 213 is configured to receive aldehyde streams of varying composition, and configured to produce an alcohol stream 215 having any desired composition. In this aspect, at least one of the n-butanal (NBAL) stream 209, the isobutanal (IBAL) stream 208, and the second aldehyde stream 212 comprising 2-ethyl hexanal (EPA) can be optionally combined with the first aldehyde stream 210 prior to introduction into the alcohol production unit 213. In another aspect, the alcohol production unit 213 is configured to receive a n-butanal (NBAL) stream 209, a isobutanal (IBAL) stream 208, a second aldehyde stream 212 comprising 2-ethyl hexanal (EPA), and a third aldehyde stream 225 comprising hydroxypivaldehyde. Thus, in a further aspect, the alcohol stream 215 comprises n-butanol, isobutanol, 2-ethylhexanol, or neopentylglycol, or combinations thereof.

In a further aspect, the system comprises an alcohol separation unit 216. In a still further aspect, the alcohol separation unit 216 is configured to separate at least a portion of the alcohol stream 215 into a first alcohol substream 217, a second alcohol substream 218, and a third alcohol substream 226 comprising neopentylglycol. Depending on the composition of the alcohol stream 215 and desired downstream products, the first alcohol substream 217 and the second alcohol substream 218 will each comprise n-butanol, isobutanol, or 2-ethylhexanol, or combinations thereof.

In a further aspect, the system comprises a phthalate production unit 219 configured to receive at least one alcohol stream 217 and configured to produce a phthalate stream 220. As described herein, the phthalate production unit 219 is configured to receive alcohol streams of varying composition, and configured to produce a phthalate stream 220 having any desired composition. In one aspect, the phthalate production unit 219 is configured to receive an alcohol stream 217 comprising n-butanol, isobutanol, and 2-ethylhexanol and configured to produce a phthalate stream 220 comprising dibutyl phthalate, diisobutyl phthalate, and di-(2-ethylhexyl) phthalate. In a further aspect, the phthalate production unit 219 is configured to receive an alcohol stream 217 comprising n-butanol, isobutanol, or 2-ethylhexanol, or combinations thereof, and configured to produce a phthalate stream 220 comprising dibutyl phthalate, diisobutyl phthalate, or di-(2-ethylhexyl) phthalate, or combinations thereof.

In a further aspect, the system comprises an phthalate separation unit 221. In a still further aspect, the phthalate separation unit 221 is configured to separate at least a portion of the alcohol stream 220 into a first phthalate substream 222 and a second phthalate substream 223. Depending on the composition of the phthalate stream 215 and desired downstream products, the first phthalate substream 222 and the second phthalate substream 223 will each comprise dibutyl phthalate, diisobutyl phthalate, or di-(2-ethylhexyl) phthalate, or combinations thereof.

In various aspects, the present invention pertains to and includes at least the following aspects.

Aspect 1: A method for the simultaneous production of oxo-alcohols comprising: (a) providing a propylene stream and a syngas stream; (b) hydroformylating the propylene stream and syngas stream to produce a first aldehyde stream comprising n-butanal (NBAL) and isobutanal (IBAL); (c) aldolizing at least a portion of the NBAL to produce a second aldehyde stream comprising 2 ethylhexenal (EPA); and (d) hydrogenating simultaneously at least a portion of the first aldehyde stream and at least a portion of the second aldehyde stream to produce an alcohol stream comprising n-butanol, isobutanol, and 2-ethylhexanol; wherein step (d) is performed in a single hydrogenation reactor.

Aspect 2: The method of aspect 1, wherein the hydroformylation is performed in the presence of a hydroformylation catalyst.

Aspect 3: The method according to any preceding aspect, wherein the hydroformylation catalyst comprises a tri-phenylphosphine modified Rhodium catalyst.

Aspect 4: The method according to any preceding aspect, further comprising separating at least a portion of the first aldehyde stream into a NBAL stream and an IBAL stream.

Aspect 5: The method of aspect 4, wherein separating comprises decanting, or distillation using at least one column.

Aspect 6: The method according to any preceding aspect, wherein the first aldehyde stream comprises from greater than 0 to 100 wt % NBAL and from greater than 0 to 100 weight % IBAL.

Aspect 7: The method according to any preceding aspect, wherein the first aldehyde stream and second aldehyde stream comprise a mixed aldehyde stream.

Aspect 8: The method of aspect 7, wherein the mixed aldehyde stream comprises from greater than 0 to 100 weight % NBAL, from greater than 0 to 100 weight % IBAL, and from greater than 0 to 100 weight % EPA.

Aspect 9: The method of according to any preceding aspect, wherein the aldolization is performed in the presence of a dimerization catalyst.

Aspect 10: The method of aspect 9, wherein the condensation catalyst comprises triethylamine catalyst.

Aspect 11: The method according to any preceding aspect, wherein the hydrogenation is performed in the presence of a hydrogenation catalyst.

Aspect 12: The method according to any preceding aspect, wherein the alcohol stream comprises from greater than 0 to 100 weight % butanol, from greater than 0 to 100 weight % isobutanol, and from greater than 0 to 100 weight % 2-ethylhexanol.

Aspect 13: The method according to any preceding aspect, further comprising separating at least a portion of the alcohol stream into at least one of a butanol stream, isobutanol stream, or 2-ethylhexanol stream.

Aspect 14: The method according to any preceding aspect, further comprising esterifying the alcohol stream with phthalic acid or anhydride to produce a phthalate stream comprising dibutyl phthalate, diisobutyl phthalate, and di-(2-ethylhexyl) phthalate; wherein the esterification reaction is performed in a single esterification reactor.

Aspect 15: The method of aspect 14, wherein the phthalate stream comprises from greater than 0 to 100 weight % dibutyl phthalate, from greater than 0 to 100 weight % diisobutyl phthalate, and from greater than 0 to 100 weight % di-(2-ethylhexyl) phthalate.

Aspect 16: The method of according to any preceding aspect, wherein the esterification is performed in the presence of an esterification catalyst.

Aspect 17: The method of aspect 16, wherein the esterification catalyst comprises tetraisoproypl titanate catalyst.

Aspect 18: The method according to any preceding aspect, further comprising aldolizing at least a portion of the isobutanal (IBAL) stream with formaldehyde to produce a third aldehyde stream comprising hydroxypivaldehyde (HPA).

Aspect 19: The method of aspect 18, wherein the aldolization is performed in the presence of an amine catalyst.

Aspect 20: The method of aspect 19, wherein the amine catalyst comprises triethylamine (TEA).

Aspect 21: The method according to any of aspects 18-20, further comprising hydrogenating at least a portion of the third aldehyde stream to produce neopentylglycol.

Aspect 22: A method for the simultaneous production of oxo-alcohols and plasticizers comprising: (a) providing a propylene stream and a syngas stream; (b) hydroformylating the propylene stream and syngas stream to produce a first aldehyde stream comprising n-butanal (NBAL) and isobutanal (IBAL); (c) aldolizing at least a portion of the NBAL to produce a second aldehyde stream comprising 2 ethylhexenal (EPA); (d) hydrogenating simultaneously at least a portion of the first aldehyde stream and the second aldehyde stream to produce an alcohol stream comprising n-butanol, isobutanol, and 2-ethylhexanol; wherein the hydrogenation reaction is performed in a single catalytic reactor; and (e) esterifying the alcohol stream with phthalic acid or anhydride to produce a phthalate stream comprising dibutyl phthalate, diisobutyl phthalate, and di-(2-ethylhexyl) phthalate; wherein the esterification reaction is performed in a single catalytic reactor.

Aspect 23: A method for the simultaneous production of oxo-alcohols and plasticizers comprising: (a) providing a propylene stream and a syngas stream; (b) hydroformylating the propylene stream and syngas stream to produce a first aldehyde stream comprising n-butanal (NBAL) and isobutanal (IBAL); (c) aldolizing at least a portion of the NBAL to produce a second aldehyde stream comprising 2 ethylhexenal (EPA); (d) aldolizing at least a portion of the IBAL with formaldehyde (FA) to produce a third aldehyde stream comprising hydroxypivaldehyde (HPA); (e) hydrogenating simultaneously at least a portion of the first aldehyde stream, the second aldehyde stream, and the third aldehyde stream to produce an alcohol stream comprising n-butanol, isobutanol, and 2-ethylhexanol, and neopentylglycol; wherein the hydrogenation reaction is performed in a single catalytic reactor; and (f) esterifying the alcohol stream with phthalic acid or anhydride to produce a phthalate stream comprising dibutyl phthalate, diisobutyl phthalate, and di-(2-ethylhexyl) phthalate; wherein the esterification reaction is performed in a single catalytic reactor.

Aspect 24: A system for the simultaneous production of oxo-alcohols, the system comprising: (a) an aldehyde production unit configured to receive a propylene feed and a syngas feed and configured to produce a first aldehyde stream comprising n-butanal (NBAL) and isobutanal (IBAL); (b) an aldol condensation unit configured to receive at least a portion of the NBAL provided by the aldehyde production unit and configured to produce a second aldehyde stream comprising 2-ethyl hexanal (EPA); and (c) an alcohol production unit configured to receive the first and the second aldehyde streams and configured to produce an alcohol stream comprising n-butanol, isobutanol, and 2-ethylhexanol.

Aspect 25: The system according to any preceding aspect, wherein the aldehyde production unit comprises a hydroformylation subunit configured to convert propylene and syngas into an aldehyde stream.

Aspect 26: The system according to any preceding aspect, wherein the hydroformylation subunit comprises a hydroformylation catalyst.

Aspect 27: The system according to any preceding aspect, wherein the hydroformylation catalyst comprises tri-phenylphosphine modified Rhodium catalyst.

Aspect 28: The system according to any preceding aspect, wherein hydroformylation subunit comprises a catalytic reactor.

Aspect 29: The system according to any preceding aspect, further comprising an aldehyde separation unit configured to separate the first aldehyde stream into a n-butanal (NBAL) stream and an isobutanal (IBAL) stream.

Aspect 30: The system of aspect 29, wherein the aldehyde separation unit comprises a decanter, distillation column, extraction column, extractive distillation column, catalytic distillation column, or other device for separating at least one component.

Aspect 31: The system according to any preceding aspect, wherein the aldol condensation unit comprises a condensation catalyst.

Aspect 32: The system according to any preceding aspect, wherein the alcohol production unit is configured to receive a mixed aldehyde stream.

Aspect 33: The system of aspect 32, wherein the mixed aldehyde stream comprises from greater than 0 to 100 weight % NBAL, from greater than 0 to 100 weight % IBAL, and from greater than 0 to 100 weight % EPA.

Aspect 34: The system of aspect 33, wherein the mixed aldehyde stream comprises a first aldehyde stream and a second aldehyde stream.

Aspect 35: The system according to any preceding aspect, wherein the alcohol stream comprises from greater than 0 to 100 weight % butanol, from greater than 0 to 100 weight % isobutanol, and from greater than 0 to 100 weight % 2-ethylhexanol.

Aspect 36: The system according to any preceding aspect, further comprising an alcohol separation unit configured to separate the alcohol stream into a first alcohol substream and a second alcohol substream.

Aspect 37: The system of aspect 36, wherein the alcohol separation unit comprises a decanter, distillation column, extraction column, extractive distillation column, catalytic distillation column, or other device for separating at least one component.

Aspect 38: The system according to any preceding aspect, further comprising a phthalate production unit configured to receive an alcohol stream and configured to produce a phthalate stream.

Aspect 39: The system of aspect 38, wherein the phthalate production unit is configured to receive a mixed alcohol stream.

Aspect 40: The system of aspects 38 or 39, wherein the phthalate stream comprises dibutyl phthalate, diisobutyl phthalate, and di-(2-ethylhexyl) phthalate.

Aspect 41: The system of any of aspects 38-40, wherein the phthalate stream comprises from 0 to 100 weight % dibutyl phthalate, from 0 to 100 weight % diisobutyl phthalate, and from 0 to 100 weight % di-(2-ethylhexyl) phthalate.

Aspect 42: The system of any of aspects 38-41, further comprising a phthalate separation unit configured to separate the phthalate stream.

Aspect 43: The system of any of aspects 38-42, wherein the phthalate separation unit comprises a decanter, distillation column, extraction column, extractive distillation column, catalytic distillation column, or other device for separating at least one component.

Aspect 44: A system for the simultaneous production of oxo-alcohols and plasticizers, the system comprising: (a) an aldehyde production unit configured to receive a propylene feed and a syngas feed and configured to produce a first aldehyde stream comprising n-butanal (NBAL) and isobutanal (IBAL); (b) an aldol condensation unit configured to receive at least a portion of the NBAL provided by the aldehyde production unit and configured to produce a second aldehyde stream comprising 2-ethyl hexanal (EPA); (c) an alcohol production unit configured to receive the first and the second aldehyde streams and configured to produce an alcohol stream comprising n-butanol, isobutanol, and 2-ethylhexanol; and (d) a phthalate production unit configured to receive the alcohol stream and configured to produce a phthalate stream comprising dibutyl phthalate, diisobutyl phthalate, and di-(2-ethylhexyl) phthalate.

Aspect 45: A system for the simultaneous production of oxo-alcohols and plasticizers, the system comprising: (a) an aldehyde production unit configured to receive a propylene feed and a syngas feed and configured to produce a first aldehyde stream comprising n-butanal (NBAL) and isobutanal (IBAL); (b) an first aldol condensation unit configured to receive at least a portion of the NBAL provided by the aldehyde production unit and configured to produce a second aldehyde stream comprising 2-ethyl hexanal (EPA); (c) an second aldol condensation unit configured to receive at least a portion of the IBAL provided by the aldehyde production unit and a formaldehyde feed; and configured to produce a third aldehyde stream comprising hydroxypivaldehyde; (d) an alcohol production unit configured to receive the first, the second, and third aldehyde streams and configured to produce an alcohol stream comprising n-butanol, isobutanol, and 2-ethylhexanol, and a glycol stream comprising neopentylglycol; and (e) a phthalate production unit configured to receive the alcohol stream and configured to produce a phthalate stream comprising dibutyl phthalate, diisobutyl phthalate, and di-(2-ethylhexyl) phthalate.

Without further elaboration, it is believed that one skilled in the art can, using the description herein, utilize the present invention. The following examples are included to provide addition guidance to those skilled in the art of practicing the claimed invention. The examples provided are merely representative of the work and contribute to the teaching of the present invention. Accordingly, these examples are not intended to limit the invention in any manner.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The materials shown in Table 1 were used to prepare the compositions described and evaluated herein.

TABLE 1

| Item | Description | Supplier |
| --- | --- | --- |
| Component 1 Isobutyraldehyde | Purity 95.8% | Al-Bayroni, Commercial plant |
| Component 2 N-Butyraldehyde | Purity 93% | Al-Bayroni, Commercial plant |
| Component 3 2-ethylhexenal | Purity 95.5% | Al-Bayroni, Commercial plant |
| Component 4 Formaldehyde | Purity 36.5% | Saudi Formaldehyde Chemical Company |
| Component 5 Triethylamine | Purity >99% | Fluka Chemicals |
| Component 6 Benzyltrimethyl ammonium hydroxide | Purity 95.5% | Fluka Chemicals |

In each of the examples described herein, the aldehyde samples were prepared by mixing all constituents in the ratio as described herein. The aldehyde mixture was prepared by mixing crude EPA, IBAL and NBAL in the ratio of 3:1:1.

In each of the examples described herein, the alcohol samples were prepared by mixing all constituents in the ratio as described herein. In the alcohol mixtures the percentages of alcohols were n-Butanol 20%, 2-EH 60% and iso-Butanol 18%.

Gas chromatography (GC) analysis of the polycondensation reaction mixture samples described herein was performed using using using Perkin Elmer 'Autosystem' gas chromatograph equipped with a flame ionization detector and a P. E. Nelson model-1022 integrator were employed. The chromatographic separation was carried out in a supelco capillary column (30 m×0.32 mm I.D) which had poly (5%-diphenyl-95%-dimethylsiloxane) as stationary phase. The column temperature was programmed from 40° C. to 200° C. at a rate of 10° C./min. The carrier gas was Helium with a column flow of 1.5 ml/min and 15 psi head pressure. The injector temperature was kept at 225° C. and the detector at 250° C. A 0.2 microliter of neat sample was injected each time into the gas chromatograph in the above set condition and the total run time was 20 minutes.

Example 1

The following representative example illustrates the performance seen in a hydrogenation reaction in accordance with the disclosed methods and systems. Specifically, Example 1 describes hydrogenation of crude EPA, IBAL and NBAL coming from industrial plant in the presence of a hydrogenation catalyst. An aldehyde mixture was prepared as described herein by mixing crude EPA, IBAL and NBAL in the ratio of 3:1:1.

2.0 gm of catalyst (70/25/5 CuO/ZnO/Aluminum oxide) was dissolved in 50 ml methanol, and loaded in a 300 ml parr reactor. The contents were then treated with hydrogen at 170° C., under pressure of 400-500 psi for approximately 2 to 3 hours. The contents were then cooled and depressurized. 10.0 g of the aldehyde mixture was added to 40 ml methanol and 10 ml water. The aldehyde mixture was then added to the reactor for testing. Hydrogenation was carried out at 170° C., under a pressure of 400-500 psi, for 2 to 3 hours. Following this time period, conversion and selectivity data based on the substrate aldehyde was determined using the hydrogenation product stream.

According to aspects of the invention, the atomic ratios of the components in the catalyst used in Example 1 can range from 0.8-1.25 of copper and 1.5-2.5 of zinc, more preferably 1.0-1.1 of copper and 1.8-2.0 of zinc. Similarly, according to other aspects of the invention, the atomic ratios of copper to aluminum is 1.0-1.5 of copper, 0.75-1.20 of aluminum, more preferably, 1.20-1.40 of copper and 0.90-1.10 of aluminum.

To determine conversion and selectivity, the resulting reaction product was analyzed by gas chromatography (GC) for residual aldehyde. Analytical data for Example 1 is provided in Table 2 below.

TABLE 2

| Component | Retention Time (Minutes) | Product (wt %) |
| --- | --- | --- |
| N-butyraldehyde | 1.8 | 0.0 |
| Isobutyraldehyde | 2.3 | 0.0 |
| 2-EPA | 4.5 | 0.0 |
| N-butanol | 3.2 | 19.4 |
| Iso-butanol | 3.9 | 18.0 |
| 2-ethylhexanol | 8.5 | 58.8 |
| Unknowns | 14.5 | 3.8 |

As the data shows, analysis of the product stream did not reveal the presence of any aldehyde. Based on the GC data, conversion of aldehyde was 100%. Furthermore, the selectivity was 100% based on the substrate aldehyde. The aldehyde percent conversion represent the amount of aldehyde reacted under the conditions employed.

The reaction including the scale-ups, was reproducible several times. The reaction was performed at 0.5 Kg and 1.0 Kg scale and the results were smilar. GC analysis did not show the presence of any unknown peaks on large scale experiments.

Example 2

The following representative example illustrates the performance seen in an esterification reaction in accordance with the disclosed methods and systems. Specifically, Example 2 describes esterification of an oxo-alcohol mixture with acid anhydride in the presence of an esterification catalyst. The following alcohol mixture was prepared as described herein having the following composition: n-Butanol 20%, 2-EH 60% and iso-Butanol 18%.

For the reaction, the alcohol mixture was added to a 3-necked 500 mL round bottom flask. A fractional distillation column with condenser and a dean-stark apparatus was attached in the central neck, a digital thermocouple inlet in the left side neck, and dropping funnel in the right side neck. Due to significant exotherm, a stoichiometric amount of phthalic anhydride was then added slowly to the flask. Next, tetraisoproypl titanate catalyst was added drop wise to the flask. The reaction mixture was then heated to 100° C., and subsequently raised to 150° C. and maintained for 3 hours until completion. Sample aliquots for GC analysis were taken from the reaction product at 3 hours. The samples were isolated by extraction with water followed by separation under vacuum distillation. GC analysis data for the 3-hour samples is provided below in Table 3.

TABLE 3

| Component | Retention Time (Minutes) | Peak Area (wt %) |
| --- | --- | --- |
| N-butanol | 3.2 | 0.5 |
| Isobutanol | 3.9 | 0.8 |
| 2-ethylhexanol | 8.5 | 1.5 |
| Diisobutylphthalate | 11.0 | 16.5 |
| Dibutyl phthalate | 16.0 | 18.3 |
| Unknown | 19.5 | 0.3 |
| Di-2-ethylhexyl phthalate | 22.5 | 58 |
| Unknown | 24.0 | 4.0 |

As seen in Table 3, the reaction product showed a high level of conversion to the desired product esters.

Example 3

The following representative example illustrates the performance seen in a esterification reaction in accordance with the disclosed methods and systems. Specifically, Example 3 describes esterification of an oxo-alcohol mixture with acid anhydride in the presence of an esterification catalyst. The following alcohol mixture was prepared as described herein having the following composition: n-Butanol 35%, 2-EH 30% and iso-butanol 35%.

The reaction of Example 3 was carried out in the same manner as described in Example 2. Sample aliquots for GC analysis were taken from the reaction product after 3 hours. GC analysis for the 3 hours sample is provided in Table 4 below.

TABLE 4

| Component | Retention Time (Minutes) | Peak Area (%) |
| --- | --- | --- |
| N-butanol | 3.2 | 0.8 |
| Isobutanol | 3.9 | 1.2 |
| 2-ethylhexanol | 8.5 | 1.9 |
| Diisobutylphthalate | 11.0 | 27.5 |
| Dibutyl phthalate | 16.0 | 29.0 |
| Unknown | 19.5 | 4.0 |
| Di-2-ethylhexyl phthalate | 22.5 | 28 |
| Unknown | 24.0 | 7.0 |

As seen in Table 4, the reaction product showed a high level of conversion to the desired product esters.

The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for the simultaneous production of oxo-alcohols comprising:
(a) providing a propylene stream and a syngas stream;
(b) hydroformylating the propylene stream and syngas stream to produce a first aldehyde stream comprising n-butanal (NBAL) and isobutanal (IBAL);
(c) aldolizing at least a portion of the NBAL to produce a second aldehyde stream comprising 2-ethylhexenal (EPA); and
(d) mixing at least a portion of the first aldehyde stream and at least a portion of the second aldehyde stream to form a mixed stream and hydrogenating simultaneously the n-butanal (NBAL), isobutanal (IBAL), and 2-ethylhexenal (EPA) in the mixed stream to produce an alcohol stream comprising n-butanol, isobutanol, and 2-ethylhexanol;
wherein the hydrogenating is performed in a single hydrogenation reactor.

2. The method of claim 1, wherein the hydroformylation is performed in the presence of a hydroformylation catalyst; and wherein the hydroformylation catalyst comprises a tri-phenylphosphine modified Rhodium catalyst.

3. The method according to claim 1, further comprising separating at least a portion of the first aldehyde stream into a NBAL stream and an IBAL stream.

4. The method of according to claim 1, wherein the aldolization is performed in the presence of a dimerization catalyst comprising triethylamine catalyst.

5. The method according to claim 1, further comprising esterifying the alcohol stream with phthalic acid or anhydride to produce a phthalate stream comprising dibutyl phthalate, diisobutyl phthalate, and di-(2-ethylhexyl) phthalate;
wherein the esterification reaction is performed in a single esterification reactor;
wherein the esterification is performed in the presence of an esterification catalyst; and
wherein the esterification catalyst comprises tetraisopropyl titanate catalyst.

6. The method according to claim 1, further comprising aldolizing at least a portion of the isobutanal (IBAL) stream with formaldehyde to produce a third aldehyde stream comprising hydroxypivaldehyde (HPA).

7. The method of claim 6, wherein the aldolization is performed in the presence of an amine catalyst, and wherein the amine catalyst comprises triethylamine (TEA).

8. The method according to claim 6, further comprising hydrogenating at least a portion of the third aldehyde stream to produce neopentylglycol.

9. The method according to claim 1, wherein the method produces the oxo-alcohols and plasticizers, the method further comprising
(e) esterifying the alcohol stream with phthalic acid or anhydride to produce a phthalate stream comprising dibutyl phthalate, diisobutyl phthalate, and di-(2-ethylhexyl) phthalate;
wherein the esterification reaction is performed in a single catalytic reactor.

10. The method according to claim 6, wherein the method produces the oxo-alcohols and plasticizers, the method further comprises
(e) wherein the hydrogenating further comprises hydrogenating simultaneously at least a portion of the first aldehyde stream, the second aldehyde stream, and the third aldehyde stream to produce the alcohol stream which further comprises neopentylglycol;
and further comprising
(f) esterifying the alcohol stream which further comprises the neopentylglycol with phthalic acid or anhydride to produce a phthalate stream comprising dibutyl phthalate, diisobutyl phthalate, and di-(2-ethylhexyl) phthalate;
wherein the esterification reaction is performed in a single catalytic reactor.

* * * * *